(12) United States Patent
Cheng et al.

(10) Patent No.: US 8,471,037 B2
(45) Date of Patent: Jun. 25, 2013

(54) DERIVATIVES HAVING VINYL GROUP AND ITS USE IN ELECTROLUMINESCENT ELEMENT

(75) Inventors: Chien-Hong Cheng, Hsinchu (TW); He-Pei Hsu, Yunlin County (TW); Ho-Hsiu Chou, Taichung (TW); Yu-Han Chen, New Taipei (TW); Yi-Hsiang Chen, Taipei (TW)

(73) Assignee: Industrial Technology Research Institute, Hsin-Chu (TW)

( * ) Notice: Subject to any disclaimer, the term of this patent is extended or adjusted under 35 U.S.C. 154(b) by 0 days.

(21) Appl. No.: 13/365,622

(22) Filed: Feb. 3, 2012

(65) Prior Publication Data
US 2013/0041153 A1  Feb. 14, 2013

(30) Foreign Application Priority Data
Aug. 12, 2011  (TW) .............................. 100128992 A

(51) Int. Cl.
*C07D 235/00* (2006.01)
(52) U.S. Cl.
USPC ...................................................... 548/301.7
(58) Field of Classification Search
None
See application file for complete search history.

(56) References Cited

U.S. PATENT DOCUMENTS

| 5,646,948 A | 7/1997 | Kobayashi et al. |
| 2003/0165715 A1 | 9/2003 | Yoon et al. |
| 2010/0148663 A1 | 6/2010 | Tsai et al. |
| 2010/0253208 A1 | 10/2010 | Cheng et al. |
| 2011/0272676 A1 | 11/2011 | Jung et al. |

FOREIGN PATENT DOCUMENTS
WO  2007/011163 A1  1/2007

OTHER PUBLICATIONS

Krebs et al. Tetrahedron Letters 42 (2001) 6753-6757.*
Hosokawa, C. et al, "Highly efficient blue electroluminescence from a distyrylarylene emitting layer with a new dopant," Appl. Phys. Lett., Dec. 25, 1995, vol. 67, No. 26, pp. 3853-3855.
Hung, W.Y. et al, "A new benzimidazole/carbazole hybrid bipolar material for highly efficient deep-blue electrofluorescence, yellow-green electrophosphorescence, and two-color-based white OLEDs," J. Mater. Chem., Aug. 3, 2010, vol. 20, pp. 10113-10119.
Jin, Y. et al, "Novel efficient blue materials with 4H-cyclopenta[def]phenanthrene for OLEDs," Synthetic Metals, 2008, vol. 158, pp. 417-424.
Lee, M.T. et al, "Highly Efficient, Deep-Blue Doped Organic Light-Emitting Devices," Adv. Mater., 2005, vol. 17, pp. 2493-2497.
Naka, S. et al, "High electron mobility in bathophenanthroline," Appl. Phys. Lett., Jan. 10, 2000, vol. 76, No. 2, pp. 197-199.
Wang, Z. et al, "Phenanthro[9,10-d]imidazole as a new building block for blue light emitting materials," J. Mater. Chem., Feb. 11, 2011, vol. 21, pp. 5451-5456.

* cited by examiner

*Primary Examiner* — Jason M Nolan
*Assistant Examiner* — Ana Z Muresan
(74) *Attorney, Agent, or Firm* — Birch, Stewart, Kolasch & Birch, LLP

(57) ABSTRACT

The present invention relates to imidazole derivatives having vinyl group represented by general formula (I) which possess electron transporting character, have a high glass transition temperature ($T_g$), and high decomposition temperature ($T_d$):

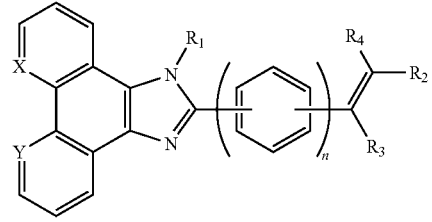

wherein all symbols are defined as recited in the specification.
The present invention also relates to a use of the imidazole derivatives having vinyl group as a guest emitter or electron transporter in luminescent elements.

20 Claims, 2 Drawing Sheets

DERIVATIVES HAVING VINYL GROUP AND ITS USE IN ELECTROLUMINESCENT ELEMENT

TECHNICAL FIELD

The disclosure relates to a imidazole derivative comprising a vinyl group and the use thereof. More particularly, this disclosure is related to a imidazole derivative which has electron transporting character and is used as the material of guest emitter or electron transport layer in a luminescent element.

BACKGROUND

Electroluminescent display is a luminescent device using solid fluorescent materials for electroluminescence. In recent practical technologies, organic materials are used as electroluminescence displays of luminescent materials. With the development of the organic electroluminescence display (OELD), producing full color display panels is one of the most important fields. Because full color display panels are consisted of three primary colors, all researchers in the art are devoted to studying luminescent materials of three primary colors.

At present, most luminescent materials, which can emit blue light disclosed in the art, are light-blue color emitting materials while the deep-blue color ones are rare. On the demand of full color OELD, the light with deep-blue color are set with a CIEx,y chromaticity coordinates of x, y<0.15 and a luminescence efficiency higher than 5 cd/A. When y is lower than 0.20, power consumption may be effectively saved and energy consumption may be substantially reduced. Thus, the development of deep-blue color luminescent materials with high efficiency is the major research topic in the field of organic light-emitting diode (OLED) currently. In addition, many scientists are devoted to the development of luminescent materials which may have a high fluorescent efficiency, balance the electron and hole mobility, and apply to single-layer organic electroluminescence element. Further, such luminescent materials may effectively reduce manufacture cost and be cost-effective to become the material of most commercial value.

During the development process of OLED technology, a host doping with a guest emitter plays a key role. Its advantages are that operating stability and efficiency of elements may be improved and light color may be adjusted by transferring excitons which is produced from excitation to dopants with high fluorescence efficiency and stability for emitting. Although many blue guest materials are continually published, doped OLED devices with high luminescence efficiency and stability are still rare.

SUMMARY

In one embodiment, an imidazole derivative comprising a vinyl group is provided and the imidazole derivative comprises a general structure represented by Formula I:

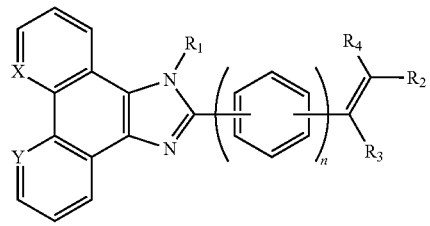

(I)

wherein, $R_1$ is selected from the group consisting of $C_{1-12}$ alkyl and $C_{6-22}$ aryl in which $C_{6-22}$ aryl is substituted or unsubstituted, wherein the substituent of $C_{6-22}$ aryl is a $C_{1-12}$ alkyl substituent;

$R_3$ and $R_4$ are the same or different groups and independently selected from the group consisting of H and $C_{1-6}$ alkyl, wherein $C_{1-6}$ alkyl is a branched or straight chain;

X and Y are the same or different groups and independently selected from the group consisting of C and N;

a dotted line represents a chemical bond or absence;

n is an integer of 1 to 10 or an integer of 1 to 2;

$R_2$ is selected from the group consisting of Formula (1), Formula (2) and Formula (3);

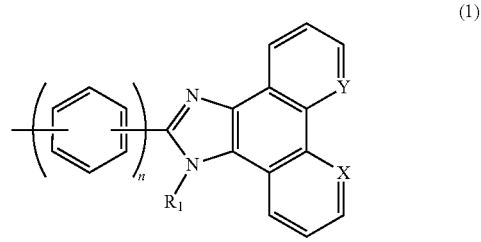

(1)

(wherein $R_1$, X, Y, n and the dotted line are defined as the above-mentioned);

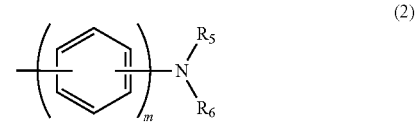

(2)

(wherein $R_5$ and $R_6$ are the same or different groups and independently represent $C_{6-10}$ aryl which is substituted with $C_{1-6}$ alkyl; or $R_5$ and $R_6$ together with N to which they are attached form the group of Formula (4);

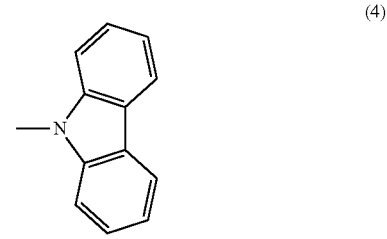

(4)

m is an integer of 0 to 10 or an integer of 0 to 2; wherein m represents two groups bound to phenylene of the repeated unit may link to the benzene ring in a ortho, meta or para position to one another. In one embodiment, two groups are linked to in a para position to one another,

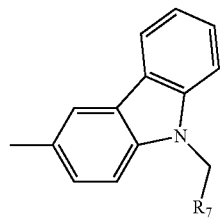

(3)

(wherein $R_7$ is selected from the group consisting of $C_{1-6}$ alkyl and phenyl).

In another embodiment, a luminescent element is provided, using the above-mentioned imidazole derivatives comprising vinyl groups as a material of guest emitter or electron transport layer in a luminescent element.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description. In the drawings.

DETAILED DESCRIPTION

Figure 1:
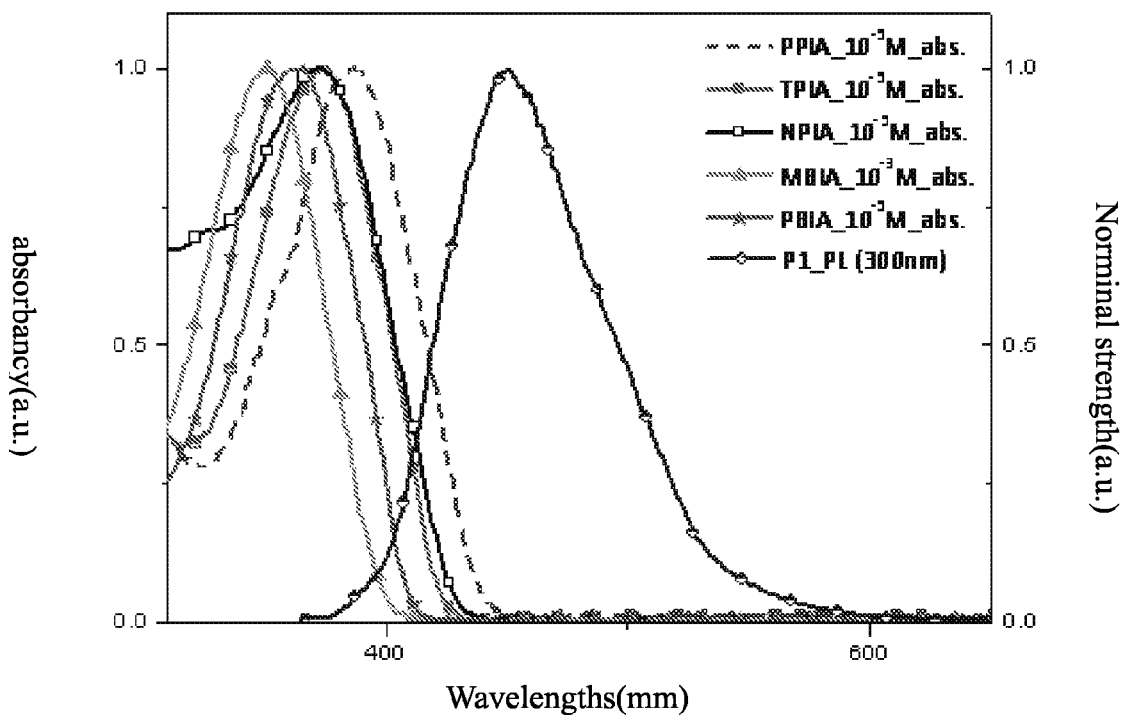
FIG. 1 illustrates the emission spectrum of compound P1 film and solution-phase absorption spectra of PPIE, TPIE and NPIE.

As described here, the term "$C_{1-12}$ alkyl" refers to an alkyl group containing one to twelve carbon atoms. In one embodiment, $R_1$ is an alkyl group containing $C_{1-6}$ alkyl, for example, methyl, ethyl, n-propyl, isopropyl, n-butyl, sec-butyl, ter-butyl, n-pentyl, neopentyl, n-hexyl or the like.

As described here, the term "$C_{1-6}$ alkyl" refers to an alkyl group containing one to six carbon atoms such as methyl, ethyl, n-propyl, isopropyl, n-butyl, sec-butyl, ter-butyl, n-pentyl, neopentyl, n-hexyl or the like. In one embodiment, $C_{1-6}$ alkyl of $R_3$, $R_4$ and $R_7$ may preferably be yl, ethyl, n-propyl, isopropyl, n-butyl, sec-butyl, or ter-butyl.

In other embodiments, $R_1$ may be $C_{6-22}$ aryl or $C_{6-10}$ aryl such as phenyl, naphthyl, acenaphthylenyl, anthranyl, phenanthryl or the like. $C_{6-22}$ aryl may optionally comprise a $C_{1-12}$ alkyl substituent which may not only be one of the exemplary groups of the above-mentioned $C_{1-6}$ alkyl, but also may be the group such as heptyl, octyl, nonyl, decyl, undecyl, dodecyl and the isomer thereof.

In one embodiment, $C_{6-10}$ aryl of $R_5$ and $R_6$ may be phenyl or naphthyl, and preferably phenyl. In other embodiments, $C_{6-10}$ aryl may optionally comprise a $C_{1-6}$ alkyl substituent which may be one of the exemplary groups of the above-mentioned $C_{1-6}$ alkyl.

In one embodiment, n represents two groups bound to phenylene of the repeated unit may link to the benzene ring in a ortho, meta or para position to one another. Preferably, two groups are linked to in a para position to one another.

In one embodiment, the imidazole derivative comprising a vinyl group is synthesized by the following method:

providing the aromatic dione compound of Formula (a), aniline and the arylcarboxaldehyde compound comprising the vinyl group of Formula (b) in an acidic condition such as acetic acid via cyclic condensation to obtain the compound of Formula (I):

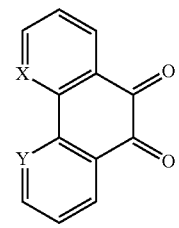

(a)

(wherein X and Y are defined as the above-mentioned);

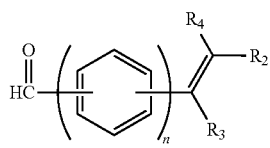

(b)

(wherein $R_2$~$R_4$ and n are defined as the above-mentioned).

The details of one or more embodiments of the disclosure are set forth in the accompanying description below. Other features and advantages of the disclosure will be apparent from the detail descriptions, and, from claims. For easily understanding the method for preparing the imidazole derivative comprising a vinyl group in the present disclosure, the imidazole derivative will be exemplarily illustrated in following examples. It is to be understood that both the foregoing general description and the following detailed description are by examples, and are intended to provide further explanation of the disclosure.

That is, the imidazole derivative comprising a vinyl group may be synthesized by the following method, which is illustrated as an example the synthesis method but not limited the scope of the disclosure. For example, in an exemplary embodiment the substituents on the benzene ring are bound in the para position, but in other embodiments may also in ortho or meta position.

Reaction Diagram 1:
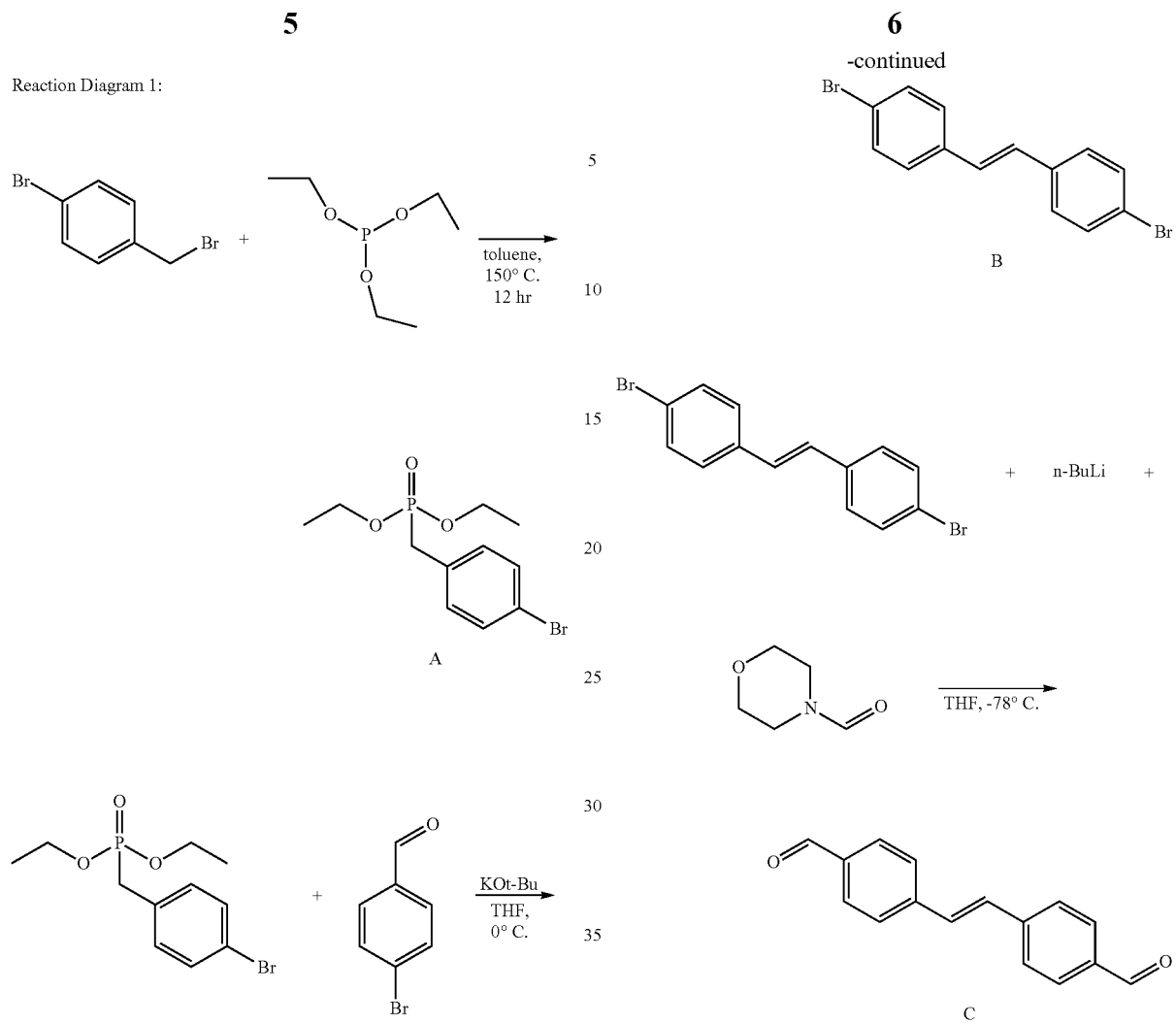

Reaction Diagram 2:
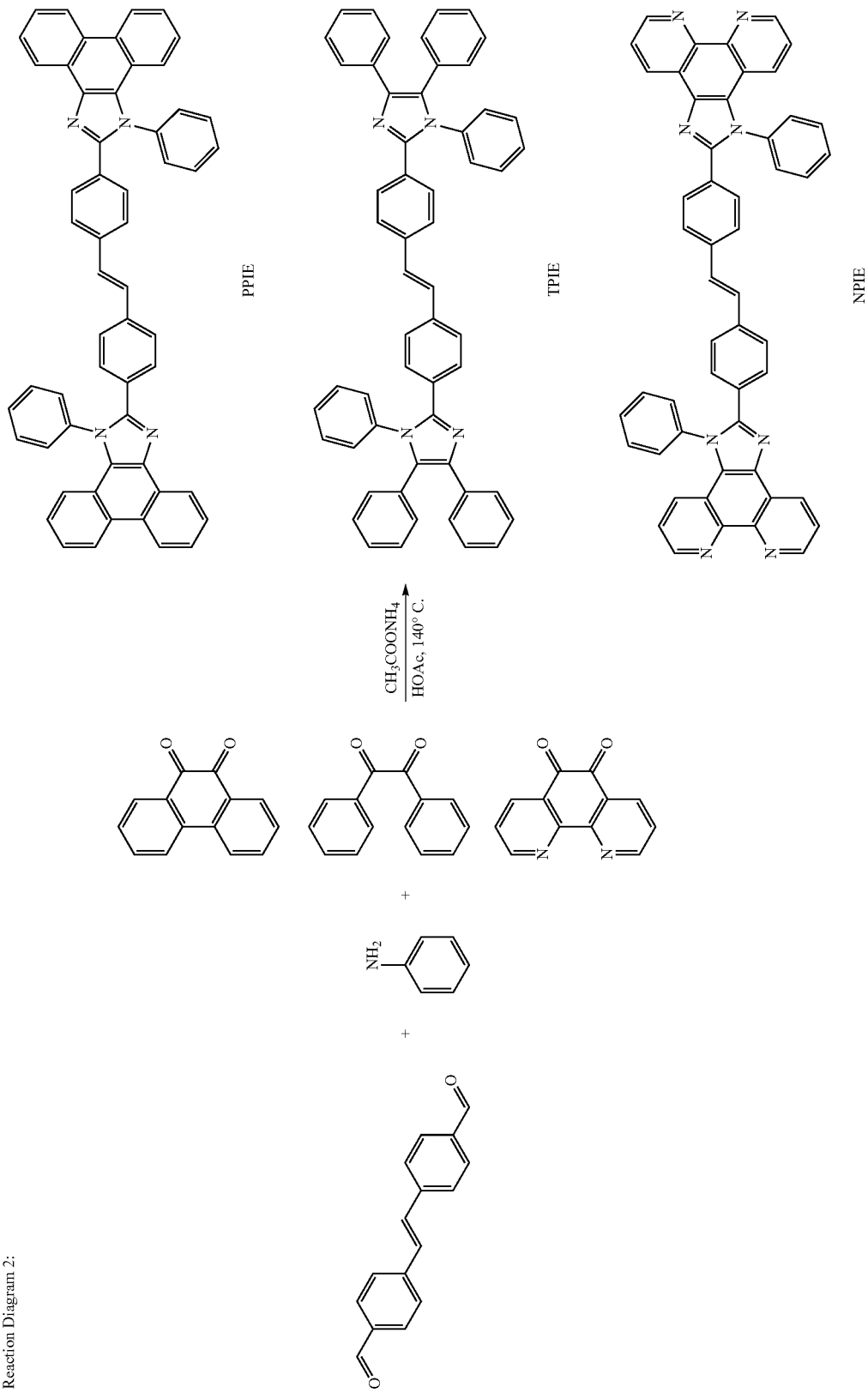

As shown in the reaction diagram 1, compound A was obtained by reacting 1-bromo-4-(bromomethyl)benzene with triethyl phosphite via Michaelis-Arbuzov reaction. Then, compound B was obtained by reacting compound A with 4-bromobenzaldehyde via Horner-Wadsworth-Emmons reaction. Further, compound B was reacted with n-BuLi in the solvent such as THF at −78° C., and then acidified with HCl aqueous solution after reacting with N-formylmorpholine to obtain the dialdehyde compound C.

As shown in the reaction diagram 2, the dialdehyde compound C, aniline and ammonium acetate then reacted with the following reactants via cyclic condensation respectively to obtain the following compounds: (1) reacting with phenanthrene-9,10-dione to obtain PPIE (E)-1,2-bis(4-(1-phenyl-1H-phenanthro-[9,10-d]imidazol-2-yl)phenyl)-ethene); (2) reacting with benzil to obtain. TPIE (E)-1,2-bis(4-(1,4,5-triphenyl-1H-imidazol-2-yl)phenyl)-ethene); (3) reacting with 1,10-phenanthroline-5,6-dione to obtain to obtain NPIE (E)-1,2-bis(4-(1-phenyl-1H-imidazo[4,5-f][1,10]-phenanthrolin-2-yl)-phenyl)ethene)). Finally, products were obtained by sublimation purification with a yield of about 23- about 65%. These three products were identified with spectrum techniques such as $^1$H-NMR, $^{13}$C-NMR, HRMS (High Resolution Mass Spectrometer) and EA (Element Analysis) to confirm the said structures of compounds.

The said 1,10-phenanthroline-5,6-dione were obtained by reacting phenanthroline with hydrochloric acid and nitric acid at high temperature via oxidation.

PREPARING EXAMPLE 1

Synthesis of 1,10-Phenanthroline-5,6-Dione

NP 1,10-phenanthroline (10.0 g, 55.5 mmol) and potassium bromide (15.0 g, 126 mmol) were in 250 ml two-neck bottle and the outlet of the condenser tube was introduced with a rubber pipe into NaOH aqueous solution. Sulfuric acid (100 mL, 98%) was poured under ice bath condition, and then fuming nitric acid (50.0 mL, 68% w/w) was added after removing ice bath. Then, the temperature was increased to 40° C. for three hours and further increased to 80~90° C. for one hour. And then, the temperature decreased and the condenser tube was removed, waiting for the dispersion of bromine gas which remained in the bottle. After 1~2 hours, the solution in the bottle was poured into ice water and NaOH aqueous solution was added slowly until pH of the mixed solution reached 6~7. At this time, a large number of yellow solid precipitations were produced, filtered with clean water and then collected as products. Finally, the yellow solids of 7.81 g with a yield of 67% were obtained by recrystallizing the said products with methanol.

$^1$H NMR (400 MHz, CDCl$_3$, δ): 9.11 (dd, J=4.4, 1.6 Hz, 2H), 8.49 (dd, J=7.6, 1.6 Hz, 2H), 7.57 (dd, J=4.8, 8 Hz, 2H), $^{13}$C NMR (100 MHz, CDCl$_3$, δ): 178.5, 156.2, 152.7, 137.1, 127.9, 125.5.

PREPARING EXAMPLE 2

Preparation of Diethyl 4-Bromobenzyl-Phosphonate (Compound A)

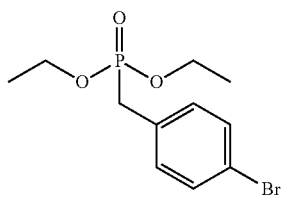

1-bromo-4-(bromomethyl)benzene (5.00 g, 20.0 mmol) was in a two-neck bottle. after introducing nitrogen gas by vacuum pumping, anhydrous toluene (80.0 mL) and triethyl phosphite (10.4 mL, 60.0 mmol) were added and heated to 150° C. for twelve hours. After the reaction finished, the solvent was removed by the rotary concentrator to obtain yellow liquid of 6.08 g (compound A) with a yield of 99%.

$^1$H NMR (400 MHz, CDCl$_3$, δ): 7.39-7.37 (m, 2H), 7.12 (dd, J=8.4 Hz, J=2.4 Hz, 2H), 3.99-3.94 (m, 4H), 3.04 (d, J=21.6 Hz, 2H), 1.21-1.18 (m, 6H)

$^{13}$C NMR (100 MHz, CDCl$_3$, 5): 131.5, 131.5, 131.4, 131.3, 130.7, 130.6, 120.8, 120.8, 62.2, 62.1, 33.8, 32.4, 16.3, 16.2.

PREPARING EXAMPLE 3

Preparation of (E)-1,2-Bis(P-Phenyl-Bromide) Ethene) (Compound B)

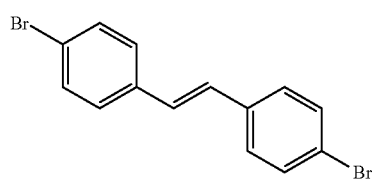

Potassium tert-butoxide (4.08 g, 36.4 mmol) was in a one-neck bottle. After introducing nitrogen gas by vacuum pumping, anhydrous tetrahydrofuran (25.0 mL) was added. Then, compound A (6.30 g, 20.0° mmol) and 4-bromobenzaldehyde (3.37 g, 18.2 mmol) were in another two-neck bottle. After introducing nitrogen gas by vacuum pumping, anhydrous tetrahydrofuran (25.0 mL) was added. The said potassium tert-butoxide and solution was added slowly under ice bath for 30 minutes. After the reaction finished and was back to room temperature, the organic layer was exacted with ethyl acetate and water respectively and collected, then removing water with magnesium sulphate and condensing. After column chromatography with n-hexane, white solids of 6.09 g with a yield of 99% were obtained.

$^1$H NMR (400 MHz, CDCl$_3$, δ): 7.46 (d, J=8.4 Hz, 2H), 7.34 (d, J=8.4 Hz, 2H), 7.00 (s, 1H).

$^{13}$C NMR (100 MHz, CDCl$_3$, δ): 135.9, 131.8, 128.1, 128.0, 121.6.

PREPARING EXAMPLE 4

Synthesis of (E)-1,2-Bis(P-Phenyl-Aldehyde)Ethene) (Compound C)

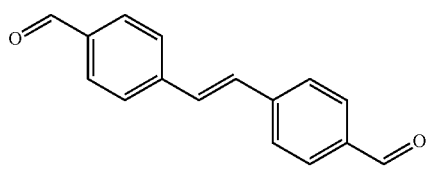

C compound B (6.00 g, 17.8 mmol) was in a reacting bottle. After heating and introducing nitrogen gas by vacuum pumping, anhydrous tetrahydrofuran (220 mL) was added and stirred to dissolve. n-BuLi (28.4 mL, 71.0 mmol, 2.50 M in n-hexane) was slowly dropped slowly after the temperature decreased to −78° C. After stirring at −78° C. for one hour, the temperature was increased to 0° C. After stirring at 0° C. for two hours, the temperature was decreased to −78° C. N-formylmorpholine was added slowly and the temperature was back to room temperature to react for eight hours, then adding diluted hydrochloric acid. After stirring for one hour, the organic layer was exacted with ethyl acetate and water respectively and collected, then removing water with magnesium sulphate and condensing. Finally, yellow solids of 2.25 g with a yield of 54% were Obtained by recrystallizing with methylene dichloride and methanol.

$^1$H NMR (400 MHz, CDCl$_3$, δ): 9.99 (s, 1H), 7.89-7.87 (m, 2H), 7.67 (d, J=8.4 Hz, 2H), 7.27 (s, 1H).
$^{13}$C NMR (100 MHz, CDCl$_3$, δ): 191.5, 142.5, 135.9, 130.7, 130.3, 127.3.

EXAMPLE 1

Synthesis of PPIE

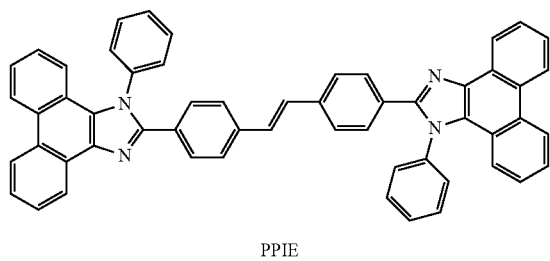 [SMILES: C(=C\c1ccc(-c2nc3c4ccccc4c4ccccc4c3n2-c2ccccc2)cc1)/c1ccc(-c2nc3c4ccccc4c4ccccc4c3n2-c2ccccc2)cc1]

PPIE phenanthrene-9,10-dione (1.06 g, 5.08 mmol), compound C (500 mg, 2.12 mmol) and CH$_3$COONH$_4$ (3.26 g, 42.3 mmol) were added into a high pressure pipe which acetic acid (28.0 mL) and aniline (0.46 mL, 5.08 mmol) then flowed into. After sealing the pipe to react in a 140° C. oil bath pot for 48 hours, the pipe cooled to room temperature and poured into water. Precipitates were produced immediately. After filtered with clean water, solids were collected as products with a yield of 85%. Finally, the said products were purified by sublimation purification with a yield of about 43% at 370° C. and 1×10$^{-5}$ torr.

$^1$H NMR (500 MHz, CDCl$_3$, δ): 8.86 (d, J=6.5 Hz, 2H), 8.76 (d, J=8.0 Hz, 2H), 8.70 (d, J=8 Hz, 2H), 7.73 (s, 2H), 7.63-7.49 (m, 16H), 7.45 (s, 2H), 7.40 (d, J=9 Hz, 4H), 7.18 (s, 4H), 7.05 (s, 2H).

The calculated value of HRMS (m/z): [M$^+$] for C$_{56}$H$_{36}$N$_4$ was 764.2940 while the measured value was 764.2947.
The calculated value of Element Analysis was C, 87.93; H, 4.74; N, 7.32 while the measured value was C, 87.15; H, 4.78; N, 7.27.

EXAMPLE 2

Synthesis of PPIE

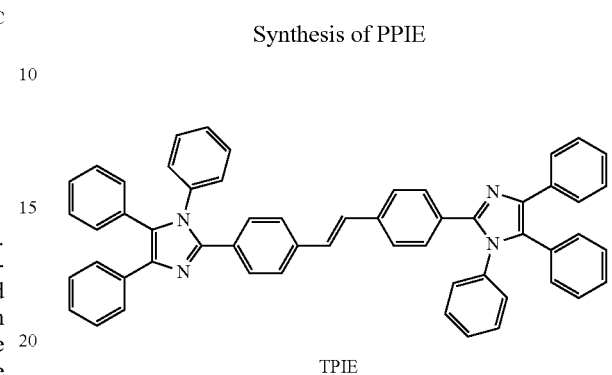

TPIE benzil (374 mg, 1.78 mmol), compound C (200 mg, 0.85 mmol) and CH$_3$COONH$_4$ (1.31 g, 16.9 mmol) were added into a high pressure pipe which acetic acid (6.0 mL) and aniline (0.19 mL, 2.03 mmol) then flowed into. After sealing the pipe to react in a 140° C. oil bath pot for 48 hours, the pipe cooled to room temperature and poured into water. Precipitates were produced immediately. After filtered with clean water, solids were collected as products with a yield of 85%. finally, the said products were purified by sublimation purification with a yield of about 65% at 330° C. and 1×10$^{-5}$ torr.

$^1$H NMR (400 MHz, CD$_2$Cl$_2$, δ): 7.58-7.55 (m, 4H), 7.44-7.38, (m, 10H), 7.34-7.16 (m, 20H), 7.13-7.11 (m, 4H), 7.07 (s, 2H).
$^{13}$C NMR (125 MHz, CDCl$_3$, δ): 146.2, 137.5, 131.1, 131.0, 129.3, 128.7, 128.4, 128.3, 128.3, 127.6, 127.1, 126.4.
The calculated value of HRMS (m/z): [M$^+$] for C$_{56}$H$_{40}$N$_4$ was 768.3253 while the measured value was 768.3251.
The calculated value of Element Analysis was C, 87.47; H, 5.24; N, 7.29 while the measured value was C, 87.43; H, 5.28; N, 7.27.

EXAMPLE 3

Synthesis of NPIE

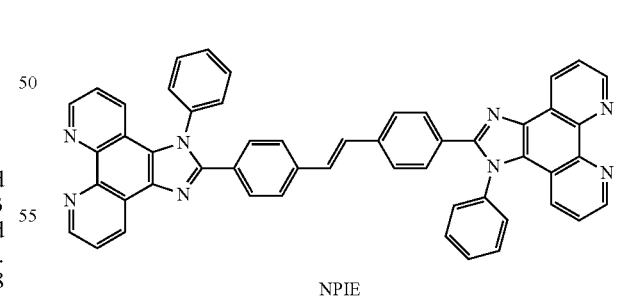

NPIE 1,10-phenanthroline-5,6-dione (1.06 g 5.08 mmol), compound C (500 mg, 2.12 mmol) and CH$_3$COONH$_4$ (3.26 g 42.3 mmol) were added into a high pressure pipe which acetic acid (28 mL) and aniline (0.46 mL 5.08 mmol) then flowed into. After sealing the pipe to react in a 140° C. oil bath pot for 48 hours, the pipe cooled to room temperature and poured into water. Precipitates were produced immediately. After filtered with clean water, solids were collected as products with a yield of 95%. Finally, the said products were purified by sublimation purification with a yield of about 32% at 382° C. and 1×10$^{-5}$ torr.

$^1$H NMR (600 MHz, CDCl$_3$, δ): 9.18 (s, 2H), 9.14 (d, J=6.6 Hz, 2H), 9.04 (s, 2H), 7.74 (s, 2H), 7.68-7.63 (m, 6H), 7.59-7.51 (m, 6H), 7.46-7.42 (m, 6H), 7.28-7.24 (m, 2H), 7.07-7.03 (m, 4H).

The calculated value of HRMS (m/z): [M$^+$] for C$_{52}$H$_{32}$N$_8$ was 768.2750 while the measured value was 768.2760.

The calculated value of Element Analysis was C, 81.23; H, 4.20; N, 14.57 while the measured value was C, 80.18; H, 4.38; N, 14.38.

COMPARED EXAMPLE 1

Synthesis of MBIE (E)-1,2-Bis(4-(1-Methyl-1H-Benzo[D]Imidazole-2-yl)-Phenyl)Ethene))

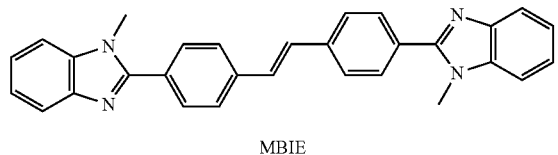 [SMILES: Cn1c(-c2ccc(/C=C/c3ccc(-c4nc5ccccc5n4C)cc3)cc2)nc2ccccc21]

MBIE

N$^1$-methyl-1,2-phenylenediamine (0.39 mL, 3.39 mmol) and compound C (200 mg, 0.85 mmol) were added into a high pressure pipe which acetic acid (20.0 mL) then flowed into. After sealing the pipe to react in a 140° C. oil bath pot for 48 hours, the pipe cooled to room temperature. the organic layer was exacted with ethyl acetate and water respectively and collected, then removing water with magnesium sulphate and condensing. after washing tan solids with a little methanol, 192 yellow solids with a yield of 52% were collected as products. Finally, the said products were purified by sublimation purification with a yield of about 23% at 250° C. and 1×10$^{-5}$ torr.

$^1$H NMR (400 MHz, CDCl$_3$, δ): 7.84-7.79 (m, 6H), 7.69 (d, J=8.4 Hz, 4H), 7.41-7.38 (m, 2H), 7.35-7.29 (m, 4H), 7.26 (s, 2H), 3.91 (s, 6H).

The calculated value of HRMS (m/z): [M$^+$] for C$_{30}$H$_{24}$N$_4$ was 440.2001 while the measured value was 440.2003.

The calculated value of Element Analysis was C, 81.79; H, 5.49; N, 12.72 while the measured value was C, 81.68; H, 5.54; N, 12.68.

COMPARED EXAMPLE 2

Synthesis of PBIE (E)-1,2-Bis(4-(1-Phenyl-1H-Benzo[D]Imidazole-2-yl)-Phenyl)Ethene))

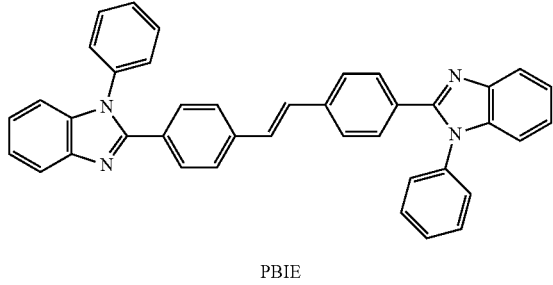 [SMILES: C(=C\c1ccc(-c2nc3ccccc3n2-c2ccccc2)cc1)/c1ccc(-c2nc3ccccc3n2-c2ccccc2)cc1]

PBIE

N$^1$-phenylbenzene-1,2-diamine (374 mg, 2.03 mmol) and compound C (200 mg, 0.85 mmol) were added into a high pressure pipe which acetic acid (10.0 mL) then flowed into. After sealing the pipe to react in a 140 oil bath pot for 48 hours, the pipe cooled to room temperature and poured into water. Precipitates were produced immediately. after filtered with a large amount of clean water, solids were collected. After washing dark green solids with a little methanol, 362 mg darked green solids with a yield of 7% were collected as products. Finally, the said products were purified by sublimation purification with a yield of about % at 280° C. and 1×10$^{-5}$ torr.

$^1$H NMR (600 MHz, CDCl$_3$, δ): 7.87 (d, J=7.8 Hz, 2H), 7.55 (d, J=7.8 Hz, 4H), 7.52-7.47 (m, 6H), 7.41 (d, J=8.4 Hz, 4H), 7.33 (d, J=6.6 Hz, 6H), 7.27-7.22 (m, 4H), 7.06 (s, 2H).

$^{13}$C NMR (150 MHz, CDCl$_3$, δ): 138.1, 137.3, 137.1, 130.0, 129.8, 129.3, 129.1, 128.8, 128.7, 127.5, 126.5, 123.5, 123.1, 120.3, 119.8, 110.4.

The calculated value of HRMS (m/z): [M$^+$] for C$_{40}$H$_{28}$N$_4$ was 564.2314 while the measured value was 564.2308.

The Study of Thermal Stability

In this study, Differential Scanning calorimetry (DSC) and Thermogravimetric Analysis (TGA) were used for measuring. DSC may measure the phase change of materials at various temperature such as glass transition temperature (T$_g$) or melting temperature (T$_m$); TGA may determine thermal stability of materials by the temperature change to the material weight. In to the preparation of OLED, the material with high T$_g$ may form the stable amorphous shape during vapor deposition. Such a formed film will not generate pin-hole defects easily. Therefore, thermal stability of materials had a great effect on the element efficiency.

Thermal properties of the above-mentioned compounds PPIE, TPIE, NPIE, MBIE and PBIE were summarized in Table 1.

TABLE 1

Thermal Properties Of PPIE, TPIE, NPIE, MBIE And PBIE

| | T$_g$ [a] (° C.) | T$_c$ [b] (° C.) | T$_m$ [c] (° C.) | T$_{d(-5\%)}$ [d] (° C.) | T$_{d(-10\%)}$ [d] (° C.) |
|---|---|---|---|---|---|
| PPIE | 190 | 255 | 401 | 497 | 512 |
| TPIE | — | — | 361, 376 | 459 | 474 |
| NPIE | — | — | — | 488 | 497 |
| MBIE | — | — | 288 | 413 | 429 |
| PBIE | — | 149 | 317 | 411 | 427 |

[a] glass transition temperature T$_g$ was measured by DSC at a heating rate of 20° C./min in N$_2$.
[b] crystalline temperature T$_c$ was measured by DSC at a heating rate of 20° C./min in N$_2$.
[c] the melting point T$_m$ was measured by DSC at a heating rate of 20° C./min in N$_2$.
[d] initial decomposition temperature T$_{d(-5\%)}$ or T$_{d(-10\%)}$ was measured by DSC at a heating rate of 20° C./min in N$_2$, which has a weight loss of 5% or 10%.

Comparing thermal properties of three compounds in Table 1, it was found that TPIE had two free-rotating benzene rings and thus its melting point (T$_m$) and thermal degradation temperature (T$_d$) was lower than PPIE. Also, T$_g$ of TPIE was not observed. Relatively, T$_g$ of PPIE was measured as 190° C. and PPIE had the highest T$_m$ (401° C.) and T$_d$ (497° C.) in homologous compounds. It showed that introducing phenanthrene groups into the molecular structures of materials may help thermal stability of materials. Such a performance was quite prominent compared with prior arts. many materials in the art such as BH-1DPA (T$_g$=110° C., 5-diphenylamine-spiro[fluorene-7,9'-benzofluorene]) and BD-1N (T$_g$=69° C., 4-[2-naphthyl-4'-(phenyl-4-vinylbenzeneamine)]-phenyl) had bad thermal stability such that elements had bad performance or failed to operate in a high voltage for a long time. Further, comparing PPIE with NPIE, it was found that T$_g$ and T$_c$ failed to be measured and lead a decrease of about 10° C. of T$_d$ when replacing the phenanthrene group of PPIE with the phenanthroline group containing nitrogen atom. Relatively, TPIE and NPIE were not easy to crystallize and T$_c$ and T$_g$ of them were not observed. In addition, T$_d$ of MBIE and PBIE in compared examples were both lower than 455° C. probably due to no rigid structures in MBIE and PBIE and their lowest molecular weights in homologous compounds. Thus, MBIE and PBIE were less stable than other materials.

Electrochemical Properties—the Measurement of Oxidation Reduction Potential

To study organic materials applied to elements, establishing energy-level diagrams was necessary for reference to choose material characters such that sites and energy-transferring effect for binding electrons with holes may be predicted.

In this experiment, the photoelectron spectrometer (AC-II) was used to measure HOMO level. Oxidation potential may be measured by AC-II. As shown in Table 2, HOMO level of PPIE, TPIE, NPIE, MBIE and PBIE was about 5.35~5.75 eV while LUMO level of them was about 2.66~3.02 eV. PPIE had a minimum bandgap and such a result corresponded to the maximum redshift in the solution-phase fluorescence emission spectrum. As shown in Table 2, PPIE had a lower HOMO level than TPIE had, inferring that PPIE had a phenanthrene with high conjugated level such that HOMO level may increase slightly, but PPIE had a less effect on LUMO level such that PPIE and TPIE had no difference in LUMO level. Then, both HOMO and LUMO level of NPIE were lower than ones of PPIE, which had a difference of 0.4 eV, inferring that withdrawing ability of NPIE may decrease both HOMO and LUMO level according to the phenanthroline group of NPIE. Finally, as shown in Table 2, the difference of HOMO level between MBIE and PBIE in compared examples was only 0.06 eV while the difference of LUMO level was also only 0.04 eV, indicating that decreasing conjugated level of the benzene ring bound on the nitrogen atom of the heterocyclic ring of imidazole had no effect on HOMO and LUMO level of molecules thereof.

TABLE 2

HOMO, LUMO And Bandgap Of PPIE, TPIE, NPIE, MBIE And PBIE Measured By CV And AC-II.

| compound | HOMO (eV) [a] | LUMO (eV) [b] | $E_S$ (eV) [c] |
|---|---|---|---|
| PPIE | 5.35 | 2.66 | 2.69(2.83) |
| TPIE | 5.47 | 2.66 | 2.81(2.95) |
| NPIE | 5.75 | 3.02 | 2.73(2.93) |
| MBIE | 5.66 | 2.75 | 2.91(3.14) |
| PBIE | 5.60 | 2.73 | 2.87(3.05) |

[a] HOMO was measured by photoelectron spectrometer (AC-II).
[b] calculated by subtracting optical bandgap of the film sample from the said HOMO.
[c] optical bandgap of the film sample; within the brackets is a value which represented the said optical bandgap obtained in $1 \times 10^{-5}$M THF.

Figure 2:
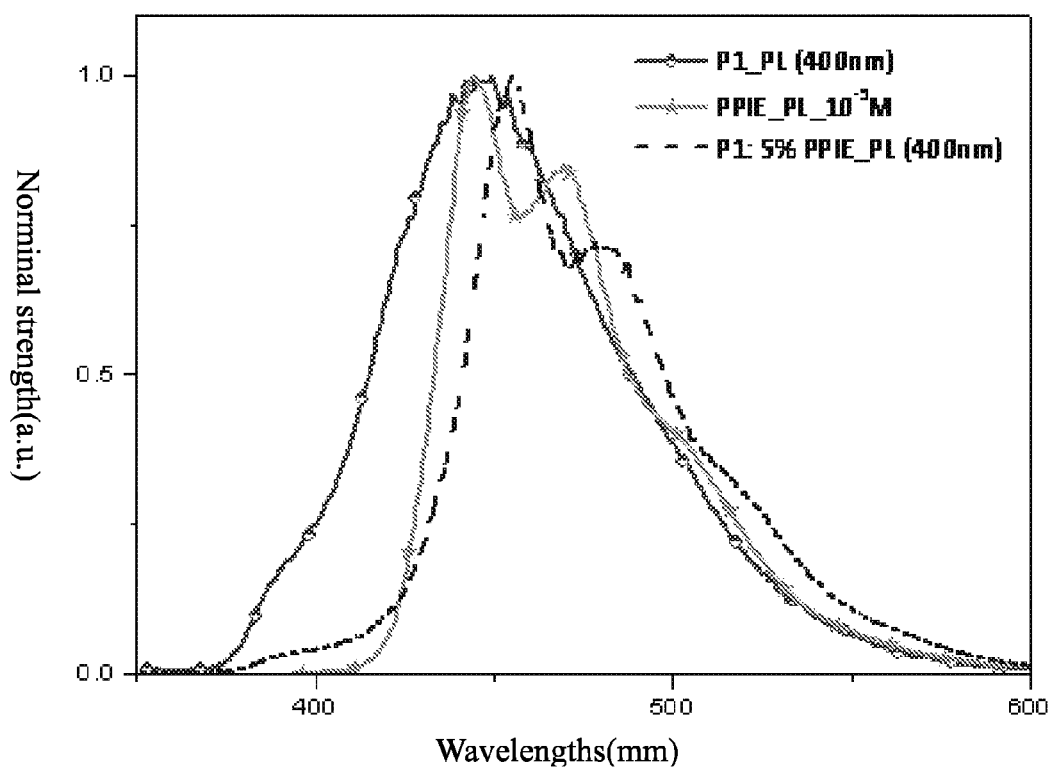
FIG. 2 illustrates emission spectra of compound P1 film, solution-phase PPIE and P1: 5% PPIE film.

The Discussion about Energy Transfer of the Guest Emitter Comprising the Imidazole Group and the Host Emitter To understand the potential for using PPIE, TPIE, NPIE, MBIE and PBIE as guest emitters, 1-(2,5-dimethyl-4-(1-pyrenyl)phenylpyrene) (DMPPP) of Formula P1 were the host emitter to compare overlapping of the light-emitting map of compound P1 and the absorption map of guest emitters. (See FIG. 1). P1: the emission spectrum of 5% PPIE film was also measured. (The film was prepared by vacuum evaporation, wherein co-evaporation was used. The preparing method was as follows: the quartz plate was fixed on a substrate, putting into the evaporator for vacuum pumping. The step of evaporating the film should start until the vacuity in the chamber reached $5 \times 10^{-6}$ Torr. The condition of evaporation was that the deposition rate between PPIE and P1 was controlled to a ratio of P1: 5% PPIE and the film thickness was 300 nm. During film coating, rotation rate of the quartz plate carrier was 20 rpm. After evaporation finished, electrodes were cooled and nitrogen gas re-inflated into the chamber to recover normal pressure. After opening the chamber, the quartz plate was taken out to determine its emission spectrum.) As shown in FIG. 2, emitting waveform of the P1: 5% PPIE emission spectrum is similar to the one of guest emitter, which emission of P1: 5% PPIE film were all originated from the guest emitter PPIE without emission of host emitter P1,

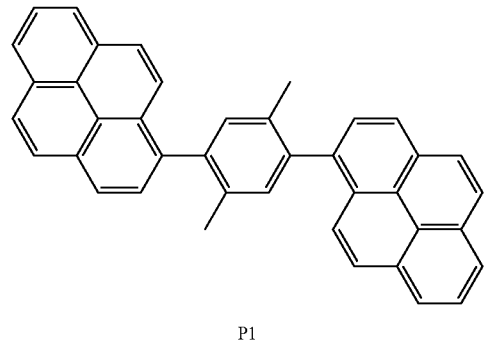 [SMILES: Cc1cc(-c2ccc3ccc4cccc5ccc2c3c45)c(C)cc1-c1ccc2ccc3cccc4ccc1c2c34 ; "P1"]

P1

Electroluminescent Properties of Electroluminescent Element

Figure 3:
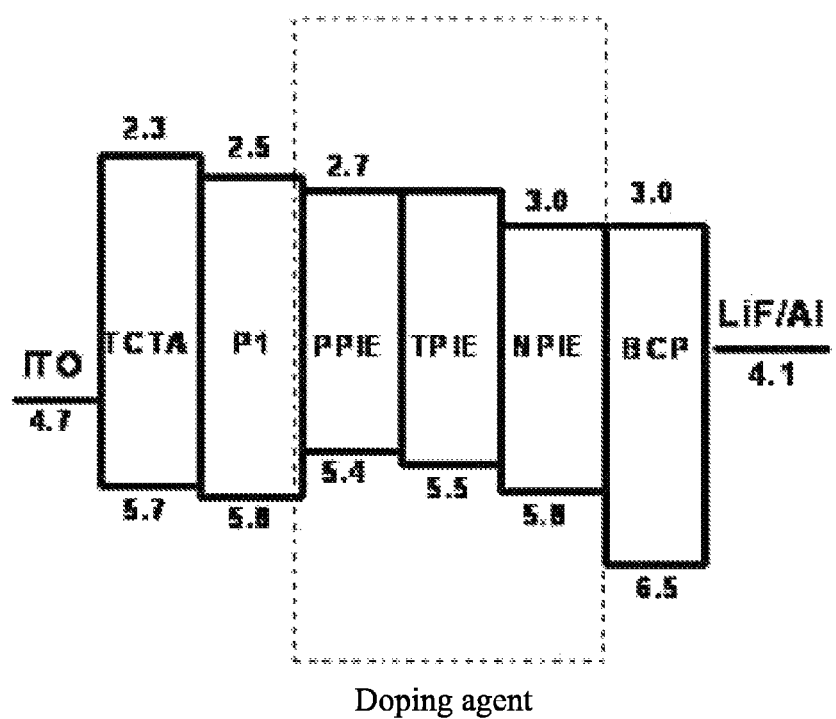
FIG. 3 illustrates schematic drawings of bandgaps of device 1A-1C.

To select the best blue fluorescent guest material, a constant element structure was applied to different guest materials to find the best one. The element structure was as follows: TCTA (50)/P1: doping agent (5%) (40)/BCP (2,9-dimethyl-4,7-diphenyl-1,10-phenanthroline) (30)/LiF (1)/Al (100), wherein TCTA (4,4',4"-tris(9-carbazoly)-triphenylamine) was the hole transport layer, P1 was a blue fluorescent host material, BCP was hole blocking layer and electron transport layer was used to prepare the element while the doping agent selected the said three imidazole derivatives (i.e. PPIE, TPIE and NPIE) as guest materials. The prepared elements were device 1A-1C respectively and schematic drawings of bandgaps thereof were illustrated in FIG. 3. Further, element efficiency thereof was showed in Table 3.

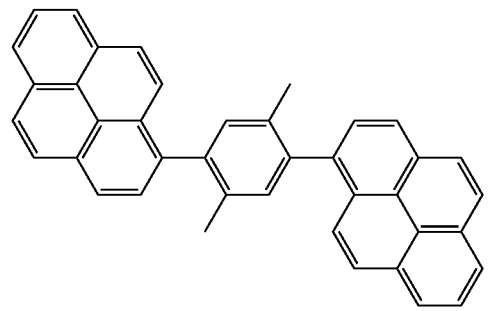

P1

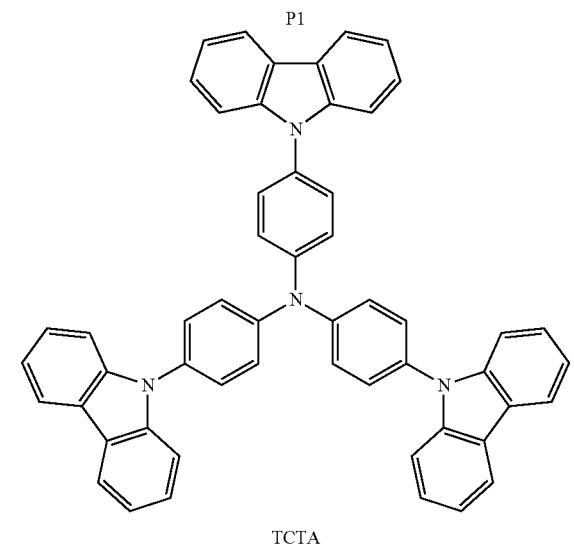

TCTA

-continued

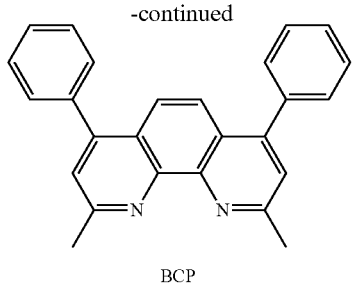

BCP

TABLE 3 optical properties and efficiency of device 1A-1C

| device[a] | $V_{on}$[c] (V) | L (cd/m$^2$, V) | $\eta_{ext}$ (%, V) | $\eta_c$ (cd/A, V) | $\eta_p$ (lm/W, V) | CIE, 8 V (x, y) | $\lambda_{max}$, 8 V (nm) |
|---|---|---|---|---|---|---|---|
| 1A | 3.5 | 50979, 16.5 | 8.2, 9.0 | 11.2, 9.0 | 5.5, 4.0 | 0.15, 0.16 | 456 |
| 1B | 4.5 | 30051, 16.0 | 7.9, 9.0 | 7.5, 9.0 | 2.7, 8.5 | 0.15, 0.10 | 442 |
| 1C | 5.0 | 28483, 17.5 | 4.9, 10.5 | 6.1, 10.5 | 2.0, 8.5 | 0.15, 0.14 | 448 |

[a] luminescence (L), external quantum efficiency($\eta_{ext}$), current efficiency ($\eta_c$) and power efficiency($\eta_p$) were maxium of the device.
[b] Applied current ($V_{on}$) to uminescence of 1 cd m$^{-2}$.
1A: ITO/TCTA (50)/P1:PPIE (5%)(40)/BCP(30)/LiF (1)/Al
1B: ITO/TCTA (50)/P1:TPIE (5%)(40)/BCP(30)/LiF (1)/Al
1C: ITO/TCTA (50)/P1:NPIE (5%)(40)/BCP(30)/LiF (1)/Al
(unit: nm)

Figure 4:
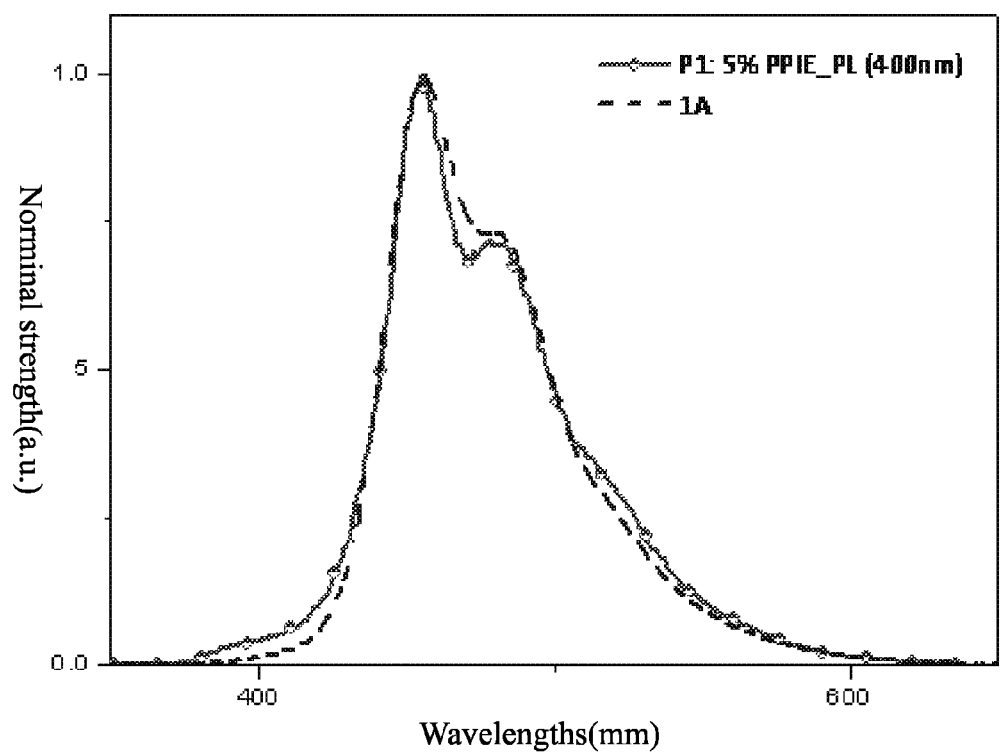
FIG. 4 illustrates drawings of PL and EL of device 1A.

Emission spectra of EL and PL of device 1A were showed in FIG. 4, wherein both spectra had the same wavelengths and waveforms, indicting that emission was generated from single-excited state molecules in emission layer. In the aspect of device performance (table 3), when the guest emitter was PPIE (1A), the performance was best and its maximum external quantum efficiency, luminescence efficiency, and luminescence power were respectively 8.2%, 11.2 cd/A and 5.5 lm/W, while drive voltage was 3.5 V and maximum luminescence reached 50979 cd/m2 with a CIEx,y chromaticity coordinates of (0.15, 0.16). Based on these data, it should be a saturated blue-light element when the guest emitter was PPIE, inferring that the excellent performance of device 1A device due to higher Förster energy transfer of PPIE and P1 and high quantum efficiency of PPIE. (see table 4). When MBIE was the guest emitter (device 1C), its maximum external quantum efficiency, luminescence efficiency, and luminescence power were 8.1%, 6.0 cd/A and 2.5 lm/W respectively, while drive voltage increased to 4.2 V and maximum luminescence reached 23785 cd/m$^2$ with a CIEx,y chromaticity coordinates of (0.15, 0.08).

TABLE 4

Solution-Phase Quantum Efficiency Of PPIE And TPIE

| sample [a] | PPIE | TPIE |
|---|---|---|
| Quantum efficiency (%) 90 | 83 | 80 |

[a] the sample was 9,10-diphenylanthracene and the solvent was cyclohexane.

In accordance with the disclosure, imidazole derivatives comprising vinyl groups were an excellent guest material for emitting blue-light, which had HOMO level of 5.35~5.75 eV, LUMO level of 2.66~3.02 eV and a considerably high $T_d$ of 459° C.~497° C. As a guest emitter material, imidazole derivatives comprising vinyl groups had excellent thermal stability, especially PPIE which further had a higher $T_g$ of 190° C. Compared with the prior art, it was a considerably excellent performance in thermal properties.

In addition, when being the guest emitting material and doped with host emitting materials, imidazole derivatives comprising vinyl groups had excellent maximum external quantum efficiency, luminescence efficiency, and luminescence power and had an ability of emitting deep-blue light. Thus, imidazole derivatives comprising vinyl groups in the disclosure was suitable for guest materials of luminescent elements.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the characteristics of the present disclosure, and without departing from the spirit and scope thereof, can make various changes and modifications of the disclosure to adapt it to various usages and conditions. Thus, other embodiments are also within the scope of the following claims.

What is claimed is:

1. An imidazole derivative consisting of the general structure represented by Formula I:

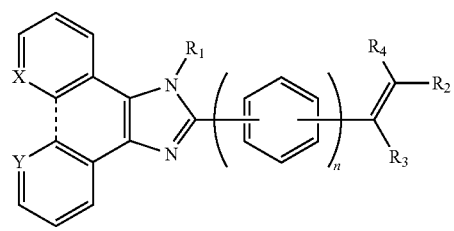

wherein,
R$_1$ is C$_{1-12}$ alkyl or C$_{6-22}$ aryl in which C$_{6-22}$ aryl is substituted or unsubstituted, wherein the substituent of the substituted C$_{6-22}$ aryl is C$_{1-12}$ alkyl;
R$_3$ and R$_4$ are the same or different and are independently H or C$_{1-6}$ alkyl, wherein C$_{1-6}$ alkyl is branched or linear;
X and Y are the same or different and are independently C and N;
a dotted line represents a chemical bond or absence;
n is an integer selected from 1 to 10;

$R_2$ is represented by Formula (1), Formula (2) or Formula (3);

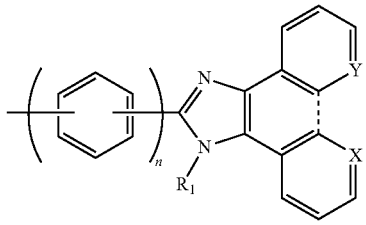
(1)

wherein $R_1$, X, Y, n and the dotted line are defined as the above-mentioned;

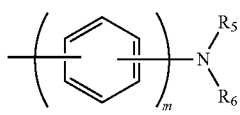
(2)

wherein $R_5$ and $R_6$ are the same or different groups and independently represent $C_{6-10}$ aryl which is substituted with $C_{1-6}$ alkyl; or $R_5$ and $R_6$ together with N to which they are attached form the group of Formula (4);

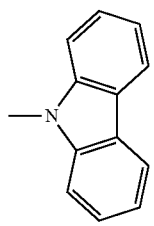
(4)

m is an integer selected from 0 to 10;

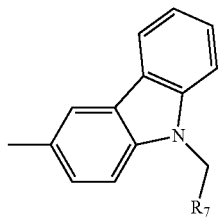
(3)

wherein $R_7$ is $C_{1-6}$ alkyl or phenyl.

2. The imidazole derivative of claim 1, wherein X and Y are each C.

3. The imidazole derivative of claim 1, wherein X and Y are each N.

4. The imidazole derivative of claim 2, wherein the dotted line represents a chemical bond, n is an integer of 2, $R_1$ is a phenyl group substituted with $C_{1-6}$ alkyl, $R_3$ and $R_4$ are each H, $R_2$ is the group of Formula (3), and $R_7$ is $C_{1-4}$ alkyl.

5. The imidazole derivative of claim 2, wherein the dotted line represents absence, n is an integer of 1, $R_1$ is a unsubstituted phenyl group or the phenyl group substituted with $C_{1-6}$ alkyl, $R_3$ and $R_4$ are each H, $R_2$ is the group of Formula (3), and $R_7$ is $C_{1-4}$ alkyl.

6. The imidazole derivative of claim 2, wherein the dotted line represents a chemical bond, n is an integer of 1 or 2, $R_1$ is a unsubstituted phenyl group or the phenyl group substituted with $C_{1-6}$ alkyl, $R_3$ and $R_4$ are each H, $R_2$ is the group of Formula (2), m is an integer of 1, $R_5$ and $R_6$ are independently the phenyl group substituted with $C_{1-4}$ alkyl.

7. The imidazole derivative of claim 2, wherein the dotted line represents absence, n is an integer of 1, $R_1$ is a unsubstituted phenyl group or the phenyl group substituted with $C_{1-6}$ alkyl, $R_3$ and $R_4$ are each H, $R_2$ is the group of Formula (1), wherein the dotted line represents a chemical bond or absence, X and Y are each C, $R_1$ is a unsubstituted phenyl group or the phenyl group substituted with $C_{1-6}$ alkyl and n is an integer of 1.

8. The imidazole derivative of claim 3, wherein the dotted line represents a chemical bond, n is an integer of 1, $R_1$ is a unsubstituted phenyl group or the phenyl group substituted with $C_{1-6}$ alkyl, $R_3$ and $R_4$ are each H, $R_2$ is the group of Formula (1), wherein the dotted line represents a chemical bond or absence, X and Y are each N, $R_1$ is a unsubstituted phenyl group or the phenyl group substituted with $C_{1-6}$ alkyl and n is an integer of 1.

9. The imidazole derivative of claim 1, wherein the imidazole derivative is used as a material of guest emitter or electron transport layer in a luminescent element.

10. A luminescent element comprising a imidazole derivative of claim 1, wherein the imidazole derivative is used as a material of guest emitter or electron transport layer in a luminescent element.

11. The imidazole derivative of claim 3, wherein the dotted line represents a chemical bond, n is an integer of 2, $R_1$ is a phenyl group substituted with $C_{1-6}$ alkyl, $R_3$ and $R_4$ are each H, $R_2$ is the group of Formula (3), and $R_7$ is $C_{1-4}$ alkyl.

12. The imidazole derivative of claim 2, wherein the imidazole derivative is used as a material of guest emitter or electron transport layer in a luminescent element.

13. The imidazole derivative of claim 3, wherein the imidazole derivative is used as a material of guest emitter or electron transport layer in a luminescent element.

14. The imidazole derivative of claim 4, wherein the imidazole derivative is used as a material of guest emitter or electron transport layer in a luminescent element.

15. The imidazole derivative of claim 5, wherein the imidazole derivative is used as a material of guest emitter or electron transport layer in a luminescent element.

16. The imidazole derivative of claim 6, wherein the imidazole derivative is used as a material of guest emitter or electron transport layer in a luminescent element.

17. The imidazole derivative of claim 7, wherein the imidazole derivative is used as a material of guest emitter or electron transport layer in a luminescent element.

18. The imidazole derivative of claim 8, wherein the imidazole derivative is used as a material of guest emitter or electron transport layer in a luminescent element.

19. A luminescent element comprising a imidazole derivative of claim 2, wherein the imidazole derivative is used as a material of guest emitter or electron transport layer in a luminescent element.

20. A luminescent element comprising a imidazole derivative of claim 3, wherein the imidazole derivative is used as a material of guest emitter or electron transport layer in a luminescent element.

* * * * *